US011215411B2

(12) United States Patent
Folk et al.

(10) Patent No.: US 11,215,411 B2
(45) Date of Patent: Jan. 4, 2022

(54) INDUCTION HEATER AND VAPORIZER

(71) Applicant: Electric Horsepower Inc., Nisku (CA)

(72) Inventors: Robert Folk, Edmonton (CA); Adrian Lachance, Red Deer (CA)

(73) Assignee: Electric Horsepower Inc., Nisku (CA)

( * ) Notice: Subject to any disclaimer, the term of this patent is extended or adjusted under 35 U.S.C. 154(b) by 649 days.

(21) Appl. No.: 15/786,261

(22) Filed: Oct. 17, 2017

(65) Prior Publication Data

US 2018/0180367 A1 Jun. 28, 2018

Related U.S. Application Data

(60) Provisional application No. 62/409,280, filed on Oct. 17, 2016.

(51) Int. Cl.

| | |
|---|---|
| ***H05B 6/10*** | (2006.01) |
| ***H05B 6/02*** | (2006.01) |
| ***A61L 2/00*** | (2006.01) |
| ***F28G 13/00*** | (2006.01) |
| ***H05B 6/36*** | (2006.01) |
| ***H05B 6/06*** | (2006.01) |
| ***F22B 1/28*** | (2006.01) |
| ***F24H 1/14*** | (2006.01) |
| ***F24H 1/10*** | (2006.01) |

(52) U.S. Cl.

CPC .............. *F28G 13/005* (2013.01); *F22B 1/28* (2013.01); *F22B 1/281* (2013.01); *F24H 1/105* (2013.01); *F24H 1/142* (2013.01); *H05B 6/06* (2013.01); *H05B 6/108* (2013.01); *H05B 6/36* (2013.01); *F24H 2250/08* (2013.01); *F28F 2280/105* (2013.01)

(58) Field of Classification Search

CPC .. H05B 6/108; H05B 6/36; H05B 6/06; F24H 1/105; F24H 1/142; F24H 2250/08; F22B 1/28; F22B 1/281; F28G 13/005; F28F 2280/105

USPC ....... 219/628–630, 632, 635, 641, 643, 650, 219/659, 665, 667, 621, 622, 624, 607, 219/654, 679, 687, 688; 99/422, 448, 99/449, 340, 403, 323.5, 323.3, DIG. 14; 422/22, 26, 27; 392/397

See application file for complete search history.

(56) References Cited

U.S. PATENT DOCUMENTS

| | | | | |
|---|---|---|---|---|
| 4,915,297 | A * | 4/1990 | Norman | B28C 7/003 122/20 A |
| 8,042,498 | B2 | 10/2011 | Hirayama et al. | |
| 2004/0182855 | A1 * | 9/2004 | Centanni | F22B 1/282 219/628 |
| 2010/0294494 | A1 * | 11/2010 | Hefley | E21B 43/267 166/272.2 |

(Continued)

FOREIGN PATENT DOCUMENTS

| | | | |
|---|---|---|---|
| JP | S597842 | A | 1/1984 |
| JP | H03194881 | A | 8/1991 |

(Continued)

*Primary Examiner* — Quang T Van

(74) *Attorney, Agent, or Firm* — Stephen M. De Klerk

(57) ABSTRACT

A method and apparatus for induction heating or vaporization of water, oil, or other fluids. An induction heater system includes a ferrous heat tube, an induction coil extending around the ferrous heat tube, an induction drive, and a controller to regulate the operation of the induction drive or a fluid supply or both, to heat or vaporize the fluid.

29 Claims, 9 Drawing Sheets

(56) References Cited

U.S. PATENT DOCUMENTS

| | | | | |
|---|---|---|---|---|
| 2011/0180531 | A1 | 7/2011 | Shinha | |
| 2012/0000642 | A1* | 1/2012 | Betzer Tsilevich | E21B 43/24 166/57 |
| 2014/0054283 | A1 | 2/2014 | Larive et al. | |
| 2014/0183025 | A1 | 7/2014 | Kamen et al. | |

FOREIGN PATENT DOCUMENTS

| | | | |
|---|---|---|---|
| JP | H09168484 | A | 6/1997 |
| JP | H1069967 | A | 3/1998 |
| JP | 2004205146 | A | 7/2004 |
| WO | 2014106386 | A1 | 7/2014 |

* cited by examiner

INDUCTION HEATER AND VAPORIZER

CROSS-REFERENCE

The present application claims the benefit of provisional patent application No. U.S. 62/409,280 filed Oct. 17, 2016, entitled "Induction Heater and Boiler".

FIELD

The present disclosure relates generally to induction heating of fluids. More particularly, the present disclosure relates to induction heating and vaporization of fluids such as water or oil or both in a vessel or conduit.

BACKGROUND

In a conventional fire tube or heat tube boiler or heater, even a slight variation off-level may result in a safety shutdown due to the fluid not being at the right level and more severe off-level conditions may result in the heat tubes running dry leading to tube damage or very dangerous run dry conditions.

To clean a fire tube boiler can be a difficult task. For example, when the fire tubes are corroded over from the minerals in the water or dirty water or other contaminants in the fluid, the efficiency of the boiler decreases significantly and it can take days or even a week to clean the boiler. This is typically done with wash guns and chemicals to remove boiler scale, and because boilers are pressure vessels, they tend to have few openings, so the cleaning is done through the limited number of hand holds and typically one manhole. If the scale build up is severe, cleaning may involve removal of a numbers of tubes, and for example if the scale build up is in the middle of the tube bundle, many or even all of the tubes may need to be removed to clean the boiler. Removal and reinstallation of the tubes may involve significant effort, including re-flaring each tube, and pressure testing.

Fire tube boiler systems also require maintenance. The refractory around the blower may also have to be replaced every few years.

Diesel fueled fired boilers may lose 30 percent or more heat out of the chimney as they tend to be less efficient, and the efficiency drops further when the fire tube corrodes or scale builds up.

In oil and gas operations, such as on drilling rigs or service rigs, where operations may be seasonal (e.g. from fall through to spring), operators tend to try run their boilers from fall through to spring without cleaning due to the significant time it takes to clean the boilers. As a result, the boilers become less efficient over the season and more fuel is burned.

It is, therefore, desirable to provide an improved heater and boiler system.

SUMMARY

It is an object of the present disclosure to obviate or mitigate at least one disadvantage of previous heater or boiler systems.

The present disclosure provides an induction heater of relatively wide application. Embodiments may be used to heat a variety of fluids, for example water or oil or combinations thereof.

The heated fluid may be used for process operations. Heated water or steam may be used for oil or gas well frac operations or other uses. Heated oil, for example heavy oil or other hydrocarbon oil, may flow more readily to facilitate conveyance down pipelines. Heated oil, for example used automotive or industrial motor oil or hydraulic oil, may be re-refined to provide petrochemical or hydrocarbon products, such as renewed automotive or industrial motor oil or renewed hydraulic oil. Heated solvent may be used for enhanced oil recovery operations. Embodiments may be used to vaporize fluids, for example water to steam or liquid solvent to vapor solvent or liquid hydrocarbons to vapor hydrocarbons. The fluids may be supplied to a dedicated heat tube or may be flowing in an existing conduit, for example a segment of process piping or a pipeline. The fluids may be heated and then conveyed to their end use, or may be heated and then stored for future use. In an embodiment disclosed, the induction heater may be used to heat asphalt (that has been pre-heated sufficiently to be conveyed through the heat tube), for example to heat the pre-heated asphalt to about 380° F. One can pre-heat the asphalt with a variety of conventional means, including air, steam, water glycol mixture, or a non-aqueous heat transfer fluid selected for asphalt heating, including but not limited to oils, synthetic and organic based formulas. One such heat transfer fluid is Globaltherm® by Global Heat Transfer Inc. In an embodiment disclosed, the heat transfer fluid has a boiling point greater than about 380° F. In an embodiment disclosed, the heat transfer fluid has a boiling point greater than a maximum heated asphalt temperature. In an embodiment disclosed, pre-heating asphalt using a heat transfer fluid and subsequently heating the asphalt with an induction heater of the present disclosure provides non-aqueous (without water) heating of asphalt, reducing or eliminating the risk of explosion/foaming which can result from contact between water-containing heating fluids and heated asphalt.

In a first aspect, the present disclosure provides an induction heater system including a ferrous heat tube, having an inlet and an outlet, an induction coil, extending around the ferrous heat tube, an induction drive, and a controller, adapted to regulate the operation of the induction drive or a fluid supply or both, wherein the fluid is conveyed through the ferrous heat tube and heated.

In an embodiment disclosed, the fluid is water or oil or combinations thereof.

In an embodiment disclosed, the ferrous heat tube is carbon steel or iron containing stainless steel or alloys thereof.

In an embodiment disclosed, the induction heater system further includes a preheater, the preheater includes a heat rising recycle, the heat rising recycle including a pump or a flow restriction or both.

In an embodiment disclosed, the fluid is heated to at least partial vaporization.

In an embodiment disclosed, the ferrous heat tube is oriented generally vertically, between about +/−45° from vertical.

In an embodiment disclosed, the inlet is located substantially at a lower portion of the ferrous heat tube and the outlet is located substantially at an upper portion of the ferrous heat tube.

In an embodiment disclosed, the induction heater system further includes one or more ferrous insert within the ferrous heat tube.

In an embodiment disclosed, the fluid supply includes a pump and an inlet accumulator or a pump and a proportional controlled electric valve.

In an embodiment disclosed, the upper outlet further includes an outlet accumulator pressure vessel or a vaporization vessel or condensing chamber.

In an embodiment disclosed, the induction heater system further includes a level instrument adapted to measure and/or indicate a liquid level in the ferrous heat tube, the controller adapted to regulate the operation of the induction drive, the fluid supply, and the liquid level.

In an embodiment disclosed, the level instrument includes a wave guided radar level or a high pressure sight glass or both.

In an embodiment disclosed, the level instrument includes a plurality of temperature transducers, extending along the ferrous heat tube to determine the liquid level.

In an embodiment disclosed, the temperature transducers include thermocouples.

In an embodiment disclosed, the induction heater system further includes a pivot mount proximate a lower end of the ferrous heat tube, wherein the ferrous heat tube is pivotable between a substantially vertical orientation and a substantially horizontal orientation about the pivot mount.

In an embodiment disclosed, the ferrous heat tube comprises seamless pipe.

In a further aspect, the present disclosure provides an induction heater system for a ferrous heat tube containing a fluid, the induction heater system including an induction coil adapted to extend substantially around the outside of the ferrous heat tube, an induction drive to drive the induction coil, and a controller, adapted to regulate the operation of the induction drive or flow of the fluid or both.

In an embodiment disclosed, the ferrous heat tube includes a portion of a pipeline, the induction coil comprises a split induction coil, adapted to be installed on the pipeline, and adapted to heat the fluid inside the pipeline, wherein the fluid includes oil, heavy oil, bitumen, diluted bitumen, paraffin wax or combinations thereof.

In a further aspect, the present disclosure provides a method of producing heated fluid, including receiving fluid from a fluid supply, conveying the fluid through a ferrous heat tube, the ferrous heat tube heated by an induction coil extending around the ferrous heat tube, to provide the heated fluid, driving the induction coil by an induction drive, and controlling the operation of the induction drive or the fluid supply or both.

In an embodiment disclosed, the fluid is water, oil, or combinations thereof.

In an embodiment disclosed, the fluid is water and the heated fluid is provided to an oil and gas well fracturing operation.

In an embodiment disclosed, the heated fluid is provided in substantially real-time.

In an embodiment disclosed, the fluid is water, and wherein the heated fluid is provided to a concrete mixing operation.

In an embodiment disclosed, the fluid is water, and wherein the water is heated to vaporization to provide steam.

In an embodiment disclosed, the steam is provided to an enhanced oil recovery process.

In an embodiment disclosed, the enhanced oil recovery process includes steam assisted gravity drainage (SAGD), cyclic steam stimulation (CSS) or variations thereof.

In an embodiment disclosed, the ferrous heat tube includes a pipeline segment, and wherein the fluid comprises oil, heavy oil, bitumen, diluted bitumen, paraffin wax or combinations thereof inside the pipeline.

In an embodiment disclosed, the fluid is used oil, and wherein the used oil is heated to vaporization to provide feedstock for an oil recycling operation.

In a further aspect, the present disclosure provides a method of descaling a substantially vertical ferrous heat tube to remove boiler scale, including cooling the heat tube down to at least a predetermined safe temperature, draining any fluid from the heat tube, activating a pre-installed induction coil to heat the ferrous heat tube to a predetermined maximum self-cleaning temperature to dry out the boiler scale, such that the boiler scale cracks and falls off the ferrous heat tube, slowly cooling the ferrous heat tube down to at least the predetermined safe temperature, and removing the boiler scale from the ferrous heat tube.

In an embodiment disclosed, the maximum predetermined self-cleaning temperature is about 1000° F.

In an embodiment disclosed, the method further includes pivoting the substantially vertical ferrous heating tube into a substantially horizontal position prior to activating the induction coil to heat the ferrous heat tube to the predetermined maximum self-cleaning temperature.

Other aspects and features of the present disclosure will become apparent to those ordinarily skilled in the art upon review of the following description of specific embodiments in conjunction with the accompanying figures.

BRIEF DESCRIPTION OF THE DRAWINGS

Embodiments of the present disclosure will now be described, by way of example only, with reference to the attached Figures.

DETAILED DESCRIPTION

Induction Heater and Vaporizer/Boiler

Generally, the present disclosure provides a method and system for induction heating or vaporization of fluids, the fluids including, but not limited to, acids, bases, chemicals in solution, hydrocarbons, glycols, water-glycol mixtures, alcohols, alcohol-water mixtures, pulps, mashes, and waxes.

Figure 1:
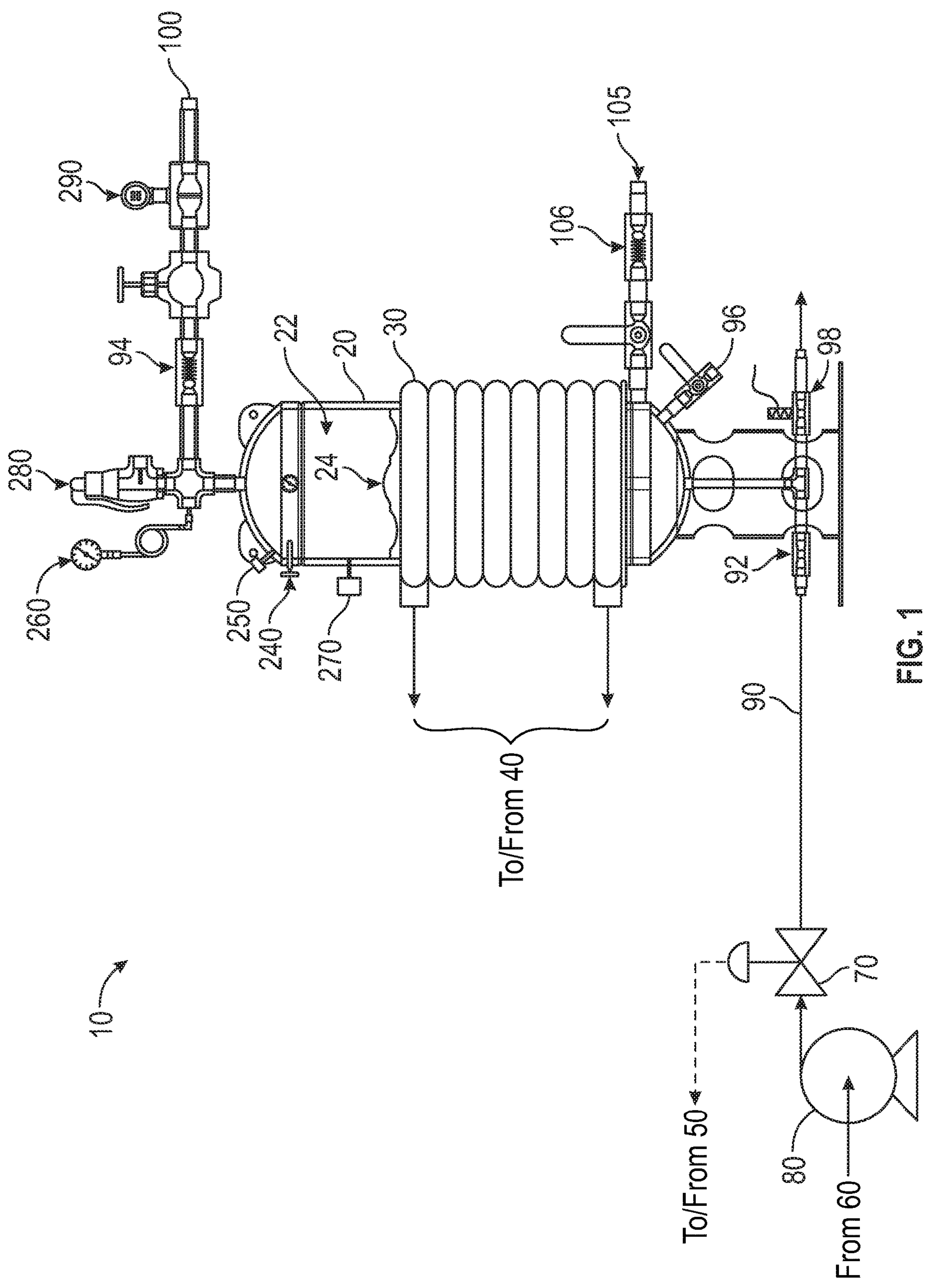
FIG. 1 is a ferrous heat tube and induction coil of the present disclosure.

Referring to FIG. 1, an induction heater system 10 includes a ferrous heat tube 20 (e.g. steel or alloys of steel to be compatible with induction heating) with an induction coil 30 extending around the ferrous heat tube 20. An induction drive 40 (see FIG. 5) drives the induction coil 30. A controller 50 (see FIG. 5) regulates the operation of the induction drive 40 or a fluid supply 60 or both.

Boiler

The fluid supply 60 may be, for example, a pressurized water source with the flowrate or pressure or both controllable by a control valve 70, for example supplied by a pump 80. Water is conveyed through the inlet 90, heated in the ferrous heat tube 20 by energy applied to the heat tube 20 by the induction coil 30, and delivered to the outlet 100. With sufficient heating, the outlet 100 is steam (i.e. vaporized water). In an embodiment disclosed, the outlet 100 is substantially saturated water, which may be subsequently flashed to produce steam.

On this type of boiler there are no internal tubes or fire tubes or fire boxes to damage if the boiler is heated too quickly, runs dry etc. The ferrous heat tube 20 is substantially vertical, but may be operated from about 90 degrees vertical to less than about 45 degrees and operate fine without shutting down. The ferrous heat tube 20 may be oriented in any orientation when heating liquids to below their boiling point, but for boiling the ferrous heat tube 20 is preferably oriented substantially vertical. With the ferrous heat tube 20 in a substantially vertical orientation, the vapors rise to the upper portion forming a steam dome or steam chamber 22 above a liquid level 24, while the liquid remains in the lower portion as the liquid (e.g. water etc.) is heated and boiled. Check valves 92, 94, 106 to permit flow in the one direction only. A blowdown valve 96 may be provided on the ferrous heat tube 20 or otherwise situated in fluid communication with the inlet 90. An automatic drain 98 is maintained in a closed position, but in the event of loss of power, automatically opens (fail open) to drain the fluid from the ferrous heat tube 20, for example if the fluid is water to avoid freezing in freezing climates. Instrumentation/transducers 115 may include one or more temperature gauge 240, one or more temperature transducer 250, one or more pressure gauge 260, one or more pressure transducer 270, one or more pressure release/safety valve 280, one or more flow meter 290, one or more level gauge 300, one or more level transducer 310, or combinations thereof.

In an embodiment disclosed, the induction heater system 10 may be used on earth drilling rigs or equipment (e.g. drilling or servicing oil and gas wells) to provide utility steam (e.g. for thawing frozen valves on frac trucks at the start of a frac job start up in the winter), or may be used for enhanced oil recovery applications (e.g. steam assisted gravity drainage (SAGD) or cyclic steam stimulation (CSS) or other processes using steam) to provide process steam or anywhere steam is used. In an embodiment disclosed, the induction heater system 10 may be used to heat a solvent for enhanced oil recovery applications (e.g. to provide heated/hot solvent or vaporized solvent enhanced oil recovery applications). In an embodiment disclosed, the induction heater system 10 may be used to heat water and solvent (either together or separately and then mixed) to produce a steam-solvent mixture for enhanced oil recovery.

The steam may be provided to a steam circulation system, such as a steam loop. In such systems, condensate is commonly returned to the boiler for re-boiling. In an embodiment disclosed, the induction heater system 10 includes a return 105 (FIG. 1) in order to accept such returned condensate into the ferrous heat tube 20 for re-boiling and circulation.

Unit Configuration

In an embodiment disclosed, the induction heater system 10 may include multiple units in parallel, for example to provide additional quantities of heated fluid (e.g. steam) or to provide redundancy for backup or servicing. In an embodiment disclosed, the induction heater system 10 may include multiple units in series, for example to divide the length of the heat tube 20 into a reduced length in order to facilitate transportation. In an embodiment disclosed, the induction heater system 10 may be provided in a portable building (e.g. on a skid). In an embodiment disclosed, two induction heater systems 10 may be provided in the portable building. In an embodiment disclosed, auxiliary equipment including a tank 160 may be provided as part of the package. In an embodiment disclosed, the package will be self-contained with an electric generator, fuel tank (for the generator), water tank 160, and the induction heater system 10.

Boiler Performance

By way of comparison of the induction heater system 10 disclosed herein to a prior art fire tube boiler: Most fire tube boiler are only allowed to be heated up at about 100° F. per hour, so it heats up evenly with the different thickness of the metal within the boiler. It can be cooled a bit quicker, but still typically takes about 45 minutes to an hour. In contrast, the induction heater system of the present disclosure can be heated up or cooled down within a short time, for example minutes, due to the only part being heated or cooled is the heat tube itself and its just one piece of relatively uniform thickness.

In terms of comparing potential performance of the induction heater system 10 of the present disclosure and a diesel fire tube boiler, for example to produce equivalent steam (pressure, rate, amount, quality):

A fire tube type 125 HP boiler used as an oilfield boiler at −40° F. ambient conditions will use approximately 4500 liters of diesel fuel per day;

An induction heater system 10 boiler of the present disclosure at −40° F. ambient conditions, powered by a diesel generator, will use about 1700 liters of diesel fuel per day.

Both types of systems would use the same water (boiler feed water) and water treatment, such as chemicals to control the pH level of the water to reduce corrosion and boiler scale. However, with an induction heater system 10 of the present disclosure, it can be taken apart and cleaned and put back together in a short period of time, for example an hour. As the heat tube is a straight piece of open pipe, a metal rotating brush cleaner can be run through/along the interior and the cleaning is completed in a short period of time. In occasions where the heat tube is severely scaled or suffers some damage or corrosion, it can be replaced in a short period of time with minimal effort.

Induction Enhancers

Figure 2:
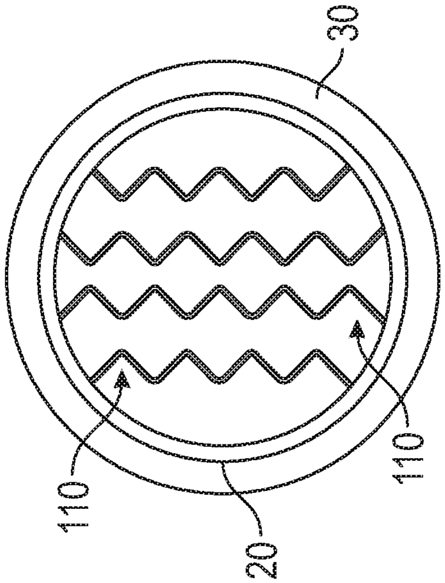
FIG. 2 is a top view of baffle plates of the present disclosure.
Figure 2B:
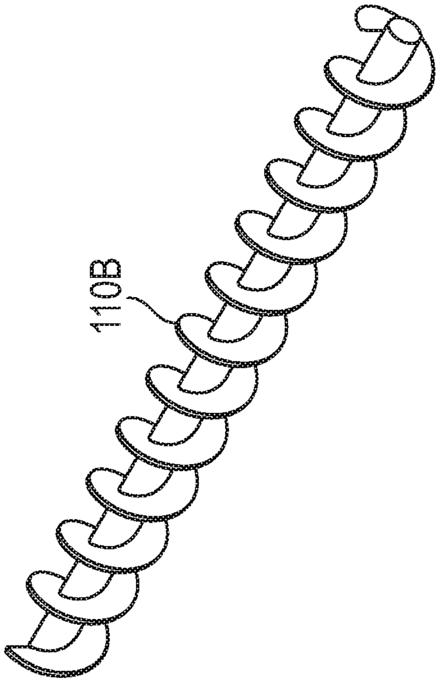
FIG. 2*b* is a perspective view of a flighting of the present disclosure.
Figure 2A:
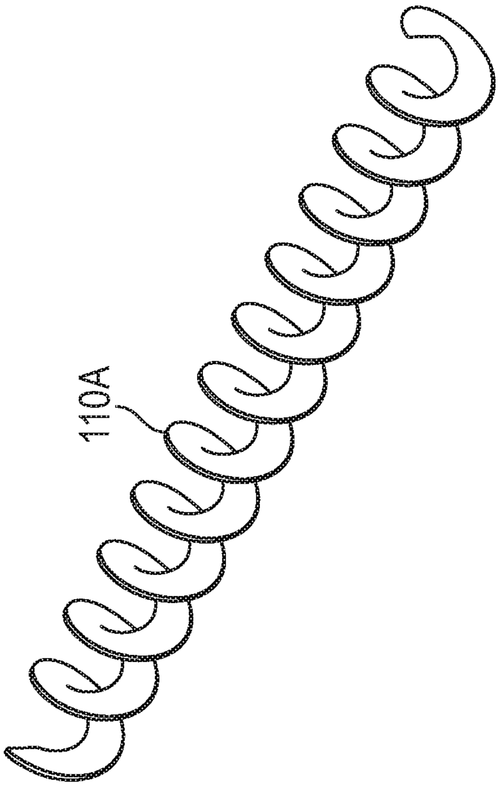
FIG. 2*a* is a perspective view of a flighting of the present disclosure.

Referring to FIG. 2, one or more ferrous insert, for example baffle plates 110 may be provided within the ferrous heat tube 20 (and within the induction coil 30) for at least a portion of the length of the heat tube 20. The ferrous insert may be a spiral flighting within the heat tube 20 (see FIGS. 2A, 2B). The flighting 110B has a central tube, whereas the flighting 110A does not. The provided additional ferrous material is heated by the induction coil 30 and thus provides additional heat transfer to the water (or other heated fluid). Preferably the baffle plate 110 or flighting 110A or flighting 110B is removable.

Figure 3A:
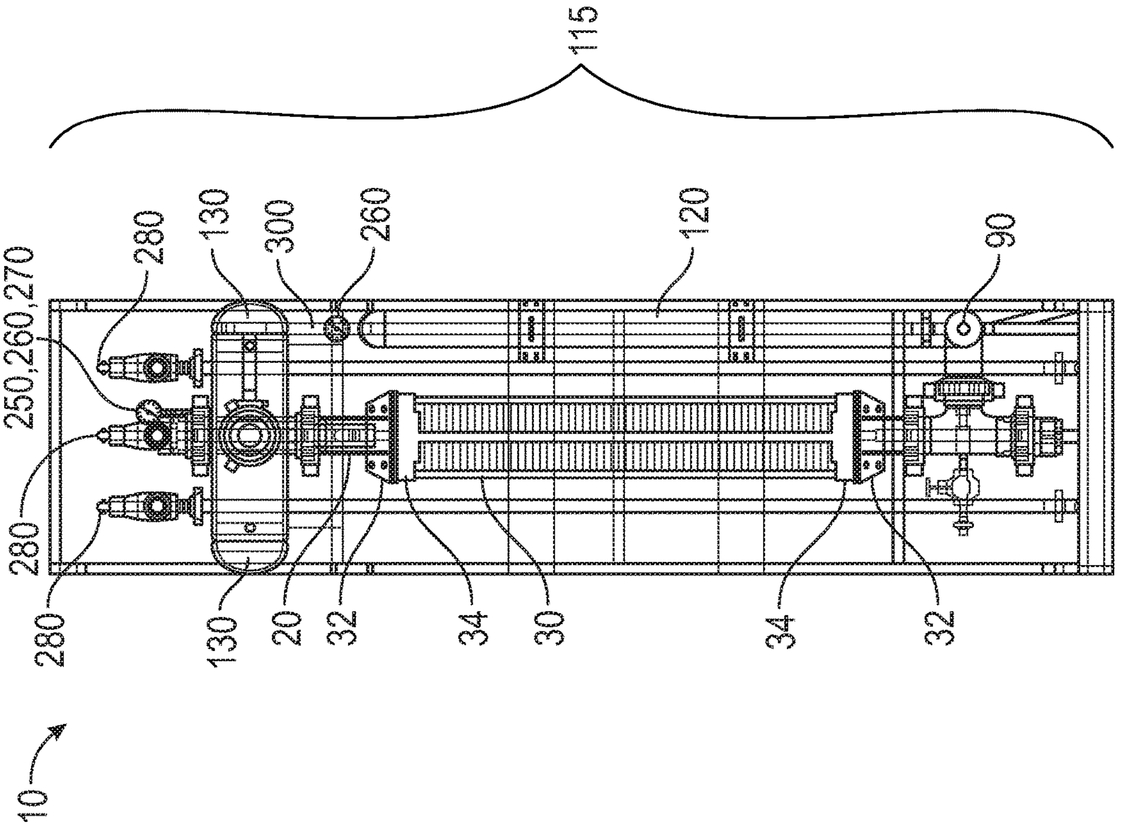
FIGS. 3-3A are an induction heater and boiler of the present disclosure.
Figure 3:
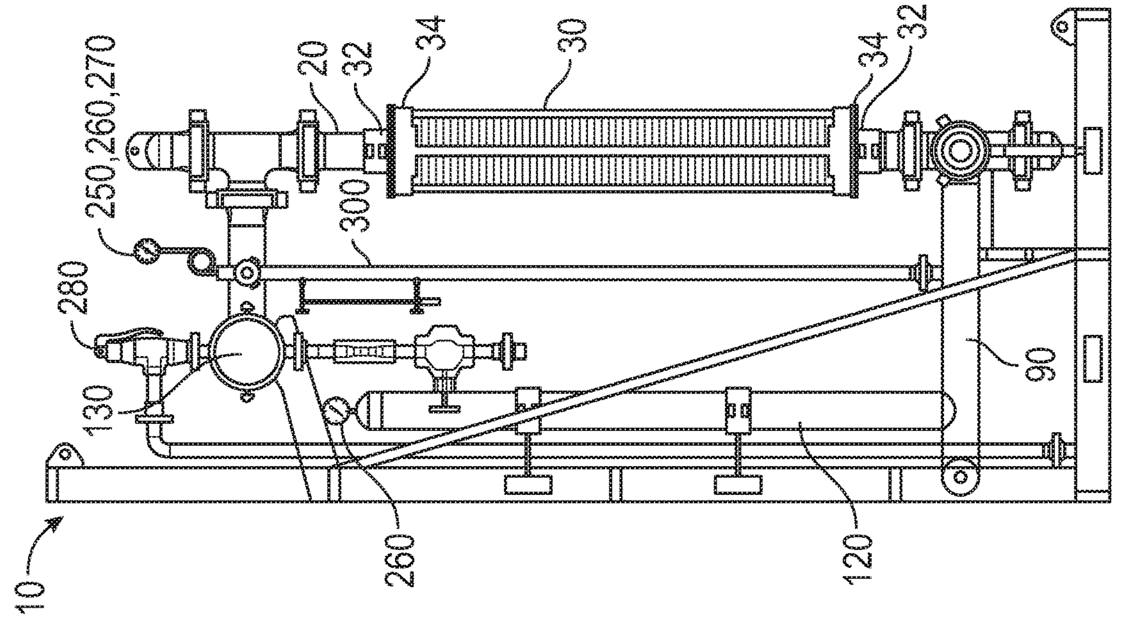

Referring to FIG. 3, the fluid supply 60 for the induction heater system 10 may include an inlet accumulator 120 and a pump 80 (see FIG. 1). The accumulator smooths out fluctuations in the system so the pump 80 (FIG. 1) does not kick in and out every couple of seconds (i.e. does not start/stop frequently). In an embodiment disclosed, the fluid supply 60 for the induction heater system 10 includes a proportional controlled electric valve instead of an accumulator 120. An outlet accumulator 130 smooths out fluctuations on the outlet side of the induction heater system 10. The fluid supply 60 may come from a pressurized water source (such as a utility water system or pressurized tank) or the fluid may be conveyed by differential pressure between the inlet 90 and the outlet 100 of the ferrous heat tube 20, in which cases the pump 80 may not be required.

The induction coil 30 may be mounted on the heat tube 20 by one or more positioning clamps 32, and insulation 34 may be provided to ensure the one or more positioning clamps 32 do not heat up from the induction field.

A liquid level is maintained in the ferrous heat tube 20 based on readings from instrumentation/transducers 115, including for example high level and low level switches (with two sets of each for redundancy as may be required by regulatory bodies in certain jurisdictions, for example in the Province of Alberta, Canada) for control of the boiler, and with a sight glass for visual confirmation of water level. Similarly, high pressure and low pressure transducers or switches or both and temperature transducers or switches or both are used for control, with temperature gauges and pressure gauges for secondary confirmation of operating conditions.

In an alternative mode of operation, the pump 80 is operated steady state at high pressure with recycle to the tank 160 to be more efficient and help heat the fluid. A proportional valve is opened proportionally to maintain a water level in the heat tube 20 at the regulated height.

On-Demand Steam Production

In an embodiment disclosed, the induction heater system 10 does not include the accumulator nor level transducers. Instead, the boiler is operated to provide on-demand real-time or near real-time steam production. The liquid level (water level) in the heat tube 20 is measured by thermocouples that measure the temperature of the water at the top of the induction coil are used. One can operate the induction heater system 10 to maintain an outlet temperature within +/−5° F. Example: If the water level starts to drop, the temperature of the heat tube 20 will start to rise up, so more water will be provided to keep the temperature at the set point. If the temperature continues to rise (despite the increase in water flow), then less power will be provided (e.g. by reducing the power going to the induction coils 30). In an embodiment disclosed, a programmable logic controller (PLC) or other controller within the Induction drive 40 receives a temperature signal and adjusts the induction coil drive electronics to increase or decrease the amount of power (kW) that the induction drive 40 sends to the induction coil 30, and a maximum allowable temperature may be set so that the system temperature cannot get too high so one cannot melt anything down or damage any equipment or take the temperature higher than a maximum allowable temperature for safety. This PLC also regulates the water level by either turning the water pump 80 on or off or by regulating a proportional control valve 70 where the water pump 80 continues to run at a set pressure 150 PSI above the steam pressure and the control valve 70 will open or close to maintain the water level or to run a stream of water to maintain the water level. This PLC also shuts off the induction drive 40 if the maximum set pressure is reached for safety or if the maximum high temperature setting is reached for safety. In an embodiment disclosed, pressures of up to 2500 psi may be used. In an embodiment disclosed, even higher pressures may be used. In an embodiment disclosed, the inlet water pressure is set at a pressure higher than the outlet steam pressure, for example about 5 percent (e.g. 2625 psi water inlet, 2500 psi steam outlet).

Control and Safety Systems

In an embodiment disclosed, the induction heater system includes safety interlocks for high temperature or high pressure or both, and as required by the laws of some jurisdictions, redundant safety interlocks may be provided.

In an embodiment disclosed, a plurality of temperature transducers may be used to measure the outlet temperature. In an embodiment disclosed, four sets of two thermocouples may be used. Each set of two thermocouples work together and the measurement of each set of thermocouple is compared to the other three sets for safety. Thus, even if a single thermocouple were to fail, the failure would be detected and the system operated or shutdown safely. Each set of two thermocouples are mounted 1" above the desired water level and 1" below the desired water level, so if the metal temperature on the heat tube starts to rise up indicating that more water is required to bring the temperature down to the normal temperature setting or if the temperature starts to fall below the set point or temperature level then the amount of water being supplied to the boiler is decreased to maintain the boiler steam output. The 1" above to 1" below range is only an example. Unlike shell and tube boilers, which require a narrow liquid level range, the induction heater system 10 of the present disclosure is able to tolerate a wider range of operating water level.

If more steam is required by opening the steam outlet valve the temperature will start to fall and the PLC will increase power to the induction drive to the induction coil to give you more power to keep the steam pressure and volume in tune with the amount the steam outlet valve is opened (up to the maximum output of the induction drive and induction coil). If the demand/use of steam is reduced, if the steam outlet valve is closed, the induction drive will regulate itself as the steam pressure gets too high or the temperature gets too high and it will simply phase itself back until it is providing no power or no kW and when the boiler steam outlet valve is re-opened and the temperature or pressure drops, the induction drive will start giving it power or kW once again to maintain the set point of the steam/water level and within the allowable pressure setting. Even if the steam outlet valve was to remain shut for an extended period of time (e.g. days) the induction drive and induction coil will continue to kick in and out to maintain the desired temperature and pressures it was set for.

The signals/measurements of each set of two thermocouples may be compared to each other (e.g. at the controller). If the thermocouples in a set of two fall out of range (e.g. more than about 15° F. from each other) a warning condition will be triggered. If the warning condition is not acknowledged/responded to within a selected time period, the induction heater system 10 will shut itself down as a safety precaution.

Steam Output

In an embodiment disclosed, the induction heater system 10 has a 120 psi working pressure, which would provide ample steam pressure for typical drilling rig or service rig boilers, which have a working pressure from about 80 psi to about 100 psi. To scale it down to a lower pressure one just needs to use a lower pressure safety valve to match the outlet pressure. For example, if the boiler pressure is 2500 psi and the inlet water is set to 2625 (5% higher than the outlet pressure) and one wanted to lower the steam pressure to 120 psi, the water inlet pressure would be lowered to about 126 psi (5% higher than the outlet pressure). Typically, safety valves are set at 10% higher than the desired steam pressure, e.g. 2750 psi for 2500 psi steam or 132 psi for 120 psi steam and so forth.

In an embodiment disclosed, the induction heater system 10 is pressure rated at about 2,500 psi and 850° F., which would provide amble steam pressure for typical injection for oil and gas extraction, for example SAGD operations. In an embodiment disclosed, the steam temperature will be around the 350° F. The heat tube itself, in particular proximate the induction coils provide the induced current/energy may see higher temperatures such as about 550° F., but it is designed for higher temperatures for caution/safety, for example it may be designed for 850° F. In an embodiment disclosed, the induction heater system 10 may be designed for 1200° F. or even 1500° F.

In an embodiment disclosed, for example, a 24 inch boiler with a short (17 inch) induction coil may generate a temperature up to about 850° F. in testing, to provide up to about 1960 kg/hour of steam. The 24 inch boiler with a longer (34 inch) induction coil may generate a temperature up to about 550° F. and may provide up to about 3000 kg/hour of steam.

In an embodiment disclosed, for example, a 6.625 inch OD/5.761 inch ID 120 psi boiler, designed for 850° F. will provide steam at least 350° F. (and preferably the heat tube 20 will not be much hotter than the steam temp of 350° F.).

If one requires more steam, the power to the induction coil 30 may be increased and the rate of water flow increased, up to a maximum of the rating of the induction coil. In an embodiment disclosed, the induction coil 30 is rated from about 0 to about 500 kW. However, induction coils 30 rated up to thousands of kW may be provided. The induction coils may range in length between about inches to about 30 feet or more.

The induction heater system 10 of the present disclosure may be used to provide superheated or wet steam, but is preferably used to provided substantially saturated steam.

Maintenance

Figure 4A:
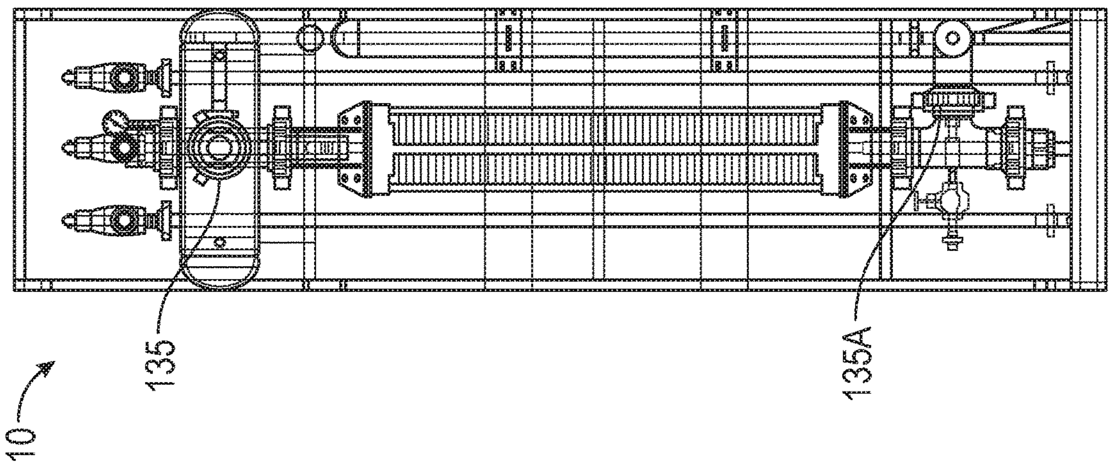
FIGS. 4-4C illustrate a cleaning sequence of the present disclosure.
Figure 4:
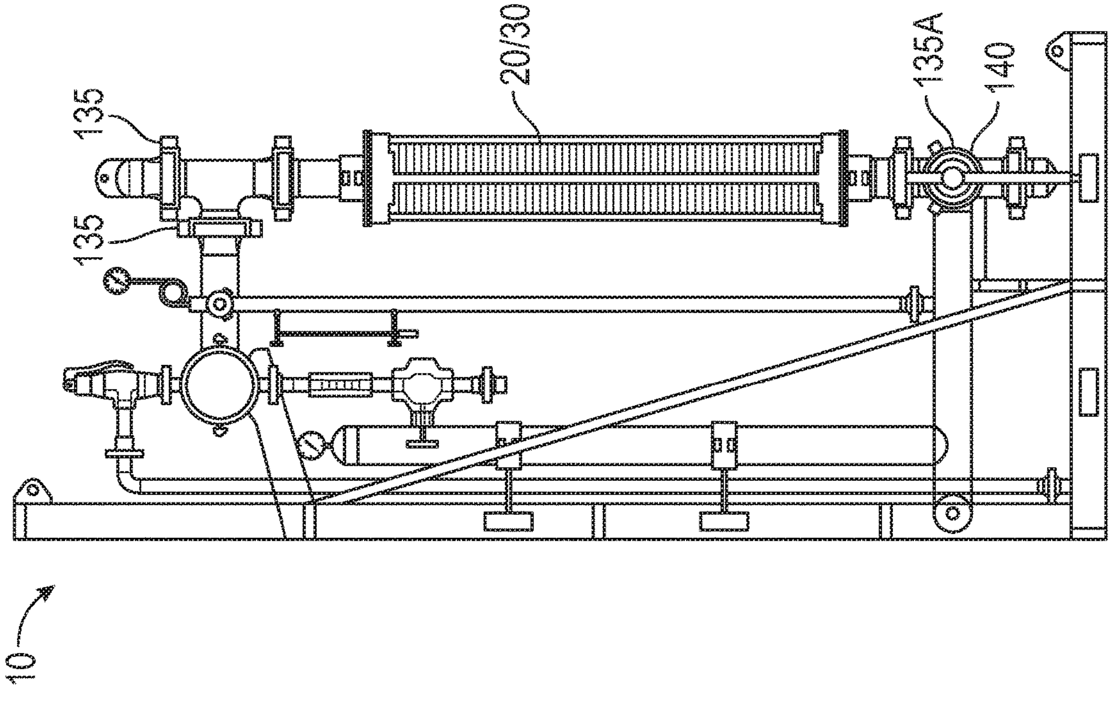
Figure 4B:
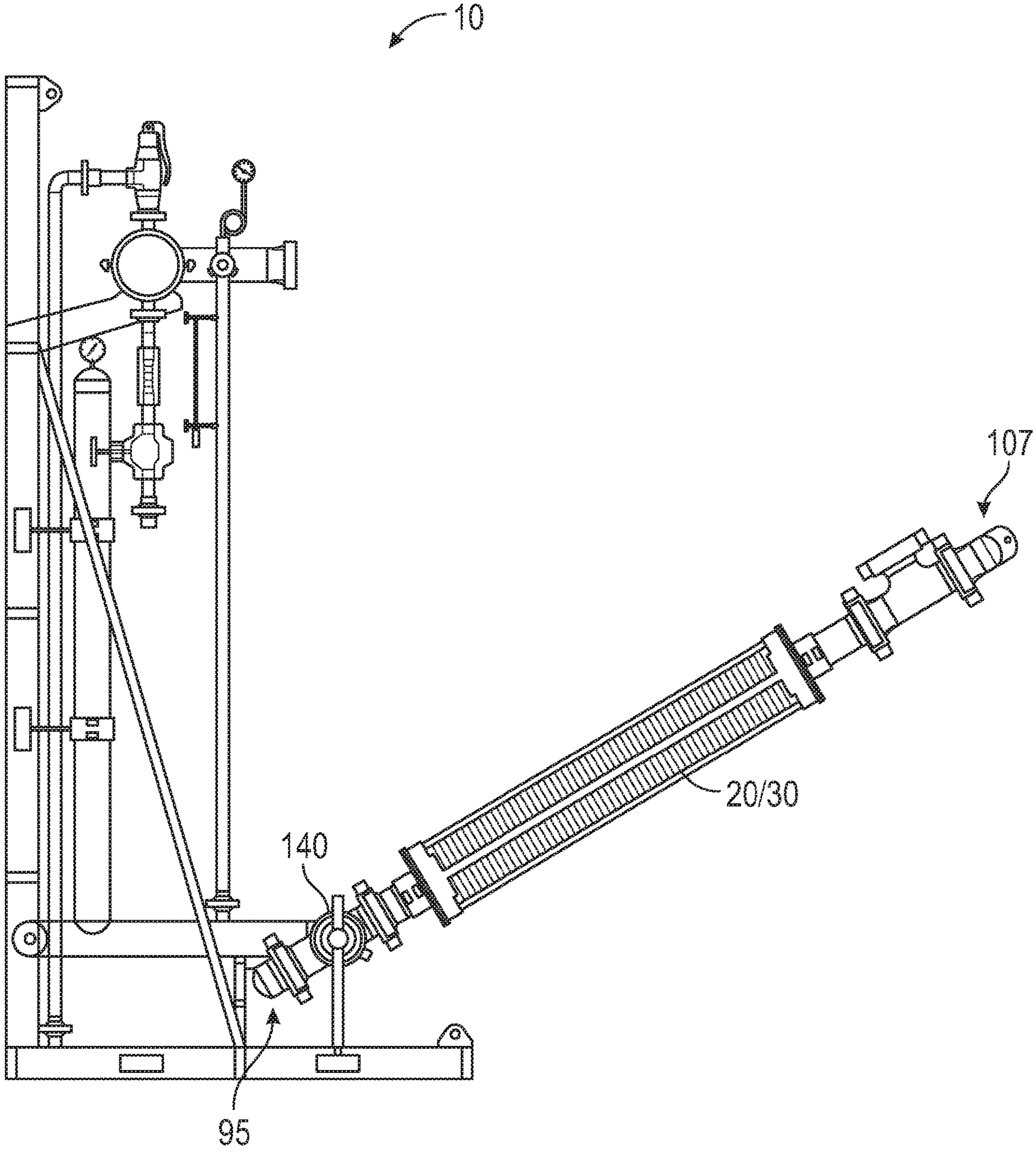

Referring to FIGS. 4-4B, in an embodiment disclosed, the ferrous heat tube 20 may be connected with releasable connectors 135 (i.e. not welded) to readily change out the ferrous heat tube 20. The releasable connectors 135 may include, for example, flanges (not shown), hammer unions (shown), Techlok® clamp connectors by Vector/Freudenberg (not shown), Gray Lock® (not shown), etc.

If for some reason the ferrous heat tube 20 gets damaged or corroded or laden with boiler scale or other impurity that cannot be cleaned, one can change out the ferrous heat tube 20 for a like sized ferrous heat tube 20 within a short time period (e.g. 2 hours), and the other parts may be re-used, like the positioning clamps, the insulation and the induction coil 30 and pressure vessel, inlet accumulator 120, outlet accumulator 130, etc.

Figure 4C:
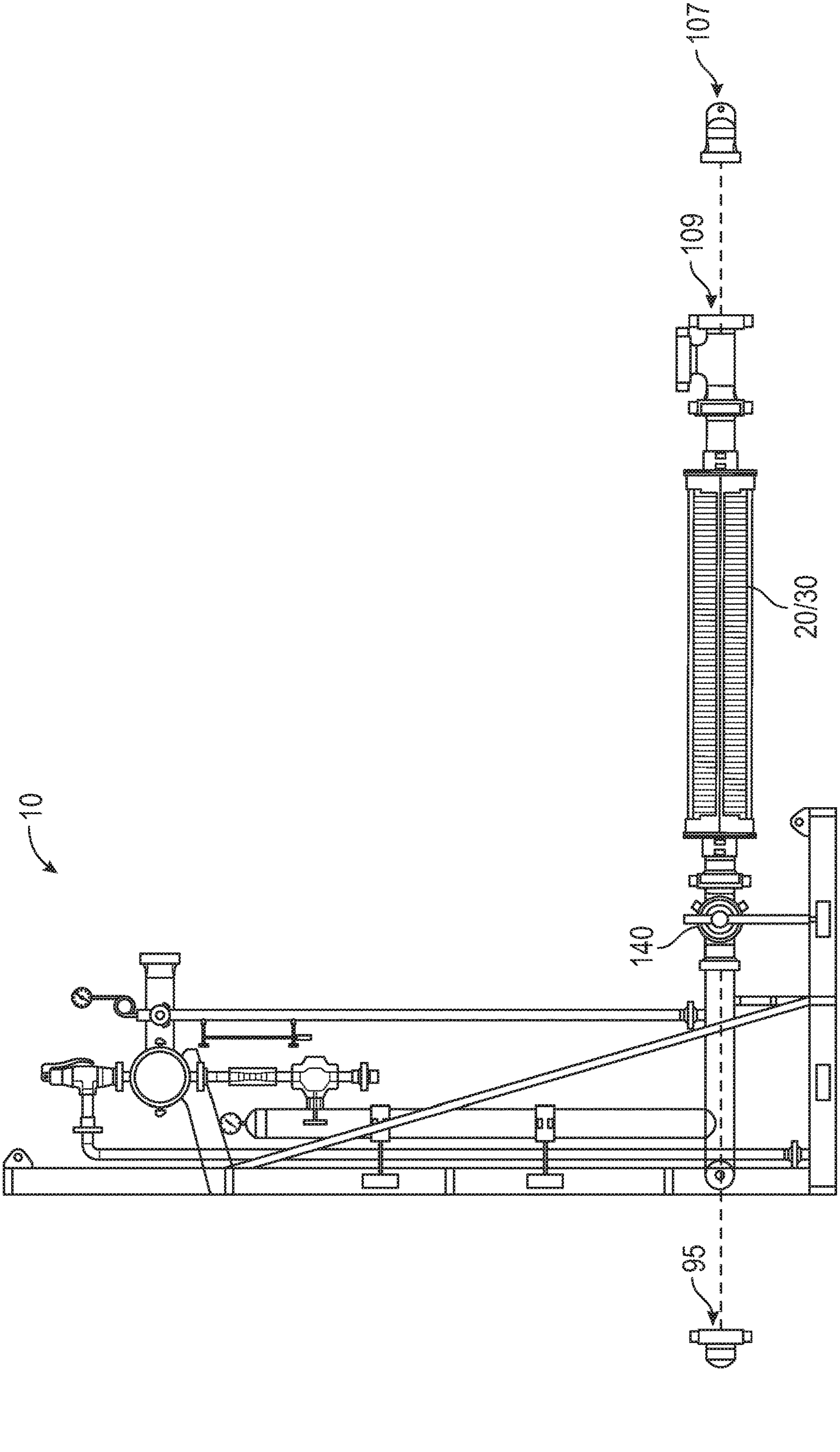

In an embodiment disclosed, the ferrous heat tube 20 may be pivotable between a substantially vertical orientation (see FIG. 4) and a substantially horizontal orientation (see FIG. 4C). A pivot 140 may be provided by a releasable connector 135A (shown) or may be provided separately from the releasable connector 135A. The releasable connector 135 may be partially released (e.g. in the case of a hammer union, knocked free, but not completely disconnected), to provide the pivot 140.

This pivotable configuration may be used to facilitate descaling to remove boiler scale that forms inside the heat tube 20. To self-clean, the heat tube 20 is depressurized and cooled to a safe temperature, the water is drained, and the heat tube 20 moved into the horizontal orientation. Activating the induction coils 30 to heat the heat tube will then dry out the boiler scale, such that the boiler scale cracks and falls off the heat tube 20. Typically, heating the heat tube to about 1000° F. is sufficient.

Once the boiler scale falls off, the heat tube 20 is slowly cooled to at least a predetermined safe temperature, and the boiler scale is removed from the heat tube 20 (for example by flushing with water or pressurized air or other known means such as mechanically removing the boiler scale with honing tools or stiff wire brushes). Removal of caps 95, 107 provide open and unobstructed access 109 to the inside of the ferrous heat tube 20 to facilitate removal of any debris. In an embodiment disclosed, the self-clean steps (e.g. heat to 1000° F., hold for a period of time, and slowly cool back to below 100° F.) may be programmed into the controller 50 to be activated by a user selection.

Induction Drive

Figure 5:
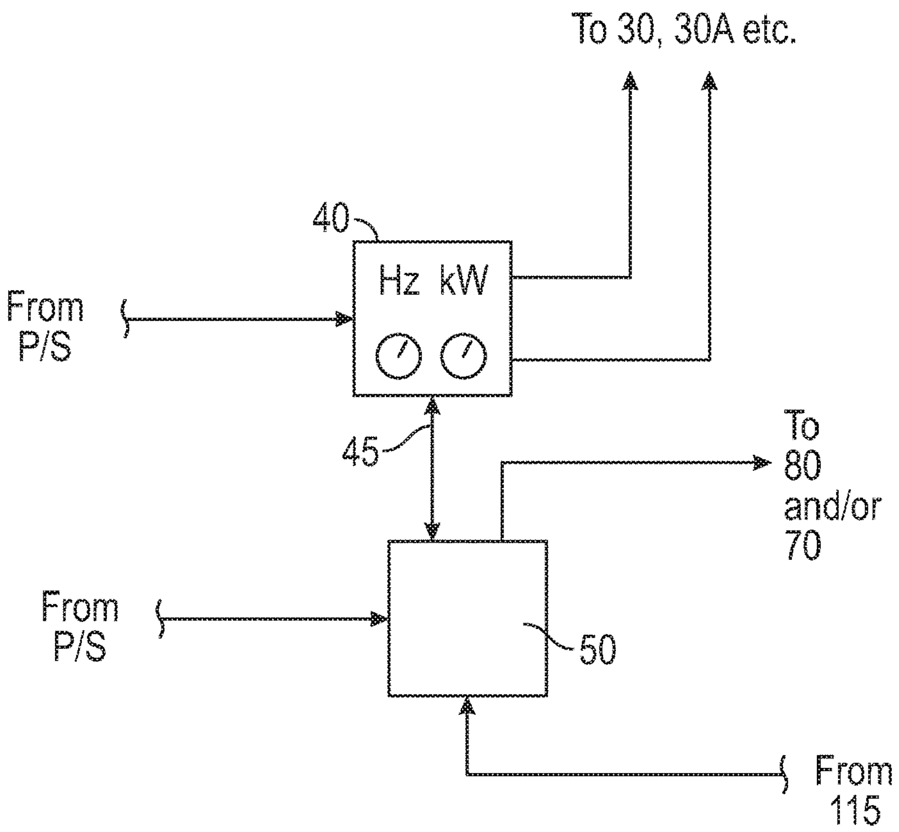
FIG. 5 is a control system of the present disclosure.

Referring to FIG. 5, the induction coils 30 are provided with an adjustable alternating current coil drive signal. The frequency (e.g. Hz) of the coil drive signal may be set or adjusted via the induction coil drive 40 to control the depth of penetration of the oscillating magnetic field and the induced eddy currents. In an embodiment disclosed, the outlet temperature (e.g. steam outlet 100) may be set, and the controller 50 adapted to maintain the set outlet temperature through programmed adjustment of the induction coil drive signal or the water supply or both (as described above). The controller 50 and the induction drive 40 are in communication by control signal/link/feedback 45.

The energy (voltage or current or kW) of the coil drive signal or the frequency of the coil drive signal or combinations thereof may be set or adjusted manually or by an automatic control system (controller 50).

The induction drive 40 drives the induction coils 30 to control the temperature or heating of the water as it passes through the heat tube 20. The induction coil drive 40 drives the induction heater coils of any frequency but the lower the frequency the deeper in the heat goes into the ferrous heat tube 20 (and if present, the baffle plates 110). For example, using a frequency of about 500 Hz provides deeper penetration than a frequency of 3000 Hz, and a frequency of 1000 Hz would provide a penetration in-between that of 500 Hz and 3000 Hz.

The induction drive 40 may preferably receive AC voltage, for example from a power line, generator, or other source (for example 480V, 3-phase, 60 Hz) and the AC voltage is rectified to provide DC voltage, and then a variable inverter is used to provide the AC coil drive signal to the induction coils. Other voltages like 120V, 230V, 380V, 575V, 600V, 2300V, 3180V, 4160V, 13,800V etc. may be used. A transformer may be used to convert the AC power source available. The induction drive 40 may drive one or more induction coils 30, for example induction coils 30, 30A, 30B (see FIG. 10), and one or more the induction coils 30A, 30B, 30C may differ in length, power capacity, driven power level, or combinations thereof.

Preheating

Figure 6:
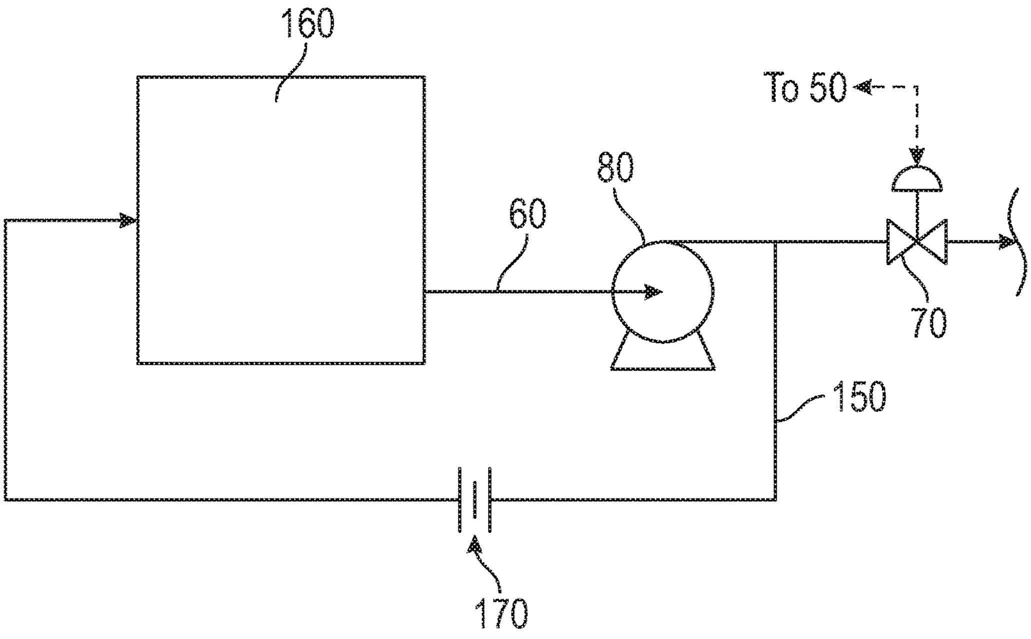
FIG. 6 is an embodiment of an induction heater system of the present disclosure.

Referring to FIG. 6, in an embodiment disclosed, a recirculation line 150 may be provided in the inlet 90 to the ferrous heat tube 20, to allow recirculation of the fluid from the outlet of the pump 80 back to a tank 160. A control valve (not shown) or flow element, such an orifice plate 170, controls or restricts the flow in the recirculation line 150. In an embodiment disclosed, for example, the orifice plate 170 may have a 60 thousands of an inch opening. When the induction heater system 10 is not producing heated fluid/steam, the fluid is allowed to circulate to some degree through the recirculation line 150. This minimum flow may reduce wear and/or on/off cycles for the pump 80. Also, pumping through the orifice plate 170 heats the water and circulating the heated water back to the tank 160 thus results in warmer (heated) inlet water to improve the efficiency of the induction heating system 10.

Figure 7:
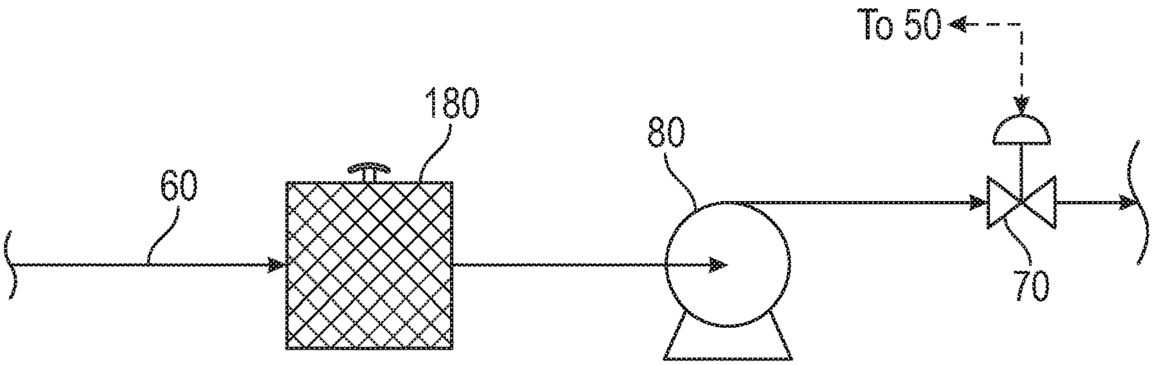
FIG. 7 is an embodiment of an induction heater system of the present disclosure.

Referring to FIG. 7, in an embodiment disclosed, a pre-heater 180 may be provided to pre-heat the fluid supply 60 before the inlet 90 of the ferrous heat tube 20. As shown, the fluid supply 60 may be pre-heated prior the pump 80, but in an alternate embodiment the fluid supply 60 may be pre-heated after the pump 80. In an embodiment disclosed, the fluid supply 60 (e.g. water in the case of the induction heater system 10 being used as a boiler) may be preheated to up to between about 150° F. to about 200° F. The pre-heater 180 feature of FIG. 7 may be combined with the recirculation line 150 feature of FIG. 6. That is, water may be circulated from the tank 160, through the pre-heater 180, through the pump 80, and back to the tank 160 via the recirculation line 150 (when the fluid supply 60 is not being directed to the ferrous heat tube 20). The pre-heater 180 may use waste heat, for example from a regular industrial engine (not shown) wherein the fluid supply 60 is used to cool the engine and is thereby heated. In the case of the marine engine, raw water cooling or open loop cooling may be used wherein the fluid supply 60 (e.g. water) is routed directly through the engine (heat exchanger) or may use closed loop cooling wherein engine coolant is circulated through the engine, and the heat is transferred from the engine coolant to the fluid supply 60 via a heat exchanger. In the case of a regular industrial engine, closed loop cooling may be used.

The engine, marine or regular industrial, may, for example, be used to drive a generator to supply at least a portion of the electricity load to the induction drive 40, the induction coil 30, the water pump 80, or combinations thereof. In another embodiment, engine exhaust waste heat, from the engine or another source may be used to pre-heat the fluid supply 60.

While the pre-heater 180 is illustrated as in the line between the tank 160 and the pump 80, the pre-heater 180 may be anywhere upstream of the heat tube 20, for example in the tank 160 or between the pump 80 and the heat tube 20.

An additional pre-heater (not shown) may also be provided in the tank 160 to pre-heat the fluid supply 60. The induction drive 40 and the induction coil 30 and interconnecting power conduits are liquid cooled by a circulated coolant, for example water or air. The heat from one or more of these items may be used to heat the fluid supply 60 (e.g. water) in the tank 160. A liquid to liquid heat exchanger (not shown) may be placed in the tank 160 and the coolant from the induction drive 40 and/or induction coil 30 will be circulated through the liquid to liquid heat exchanger within the tank 160 to help preheat the fluid supply 60 (e.g. water) to make the system more efficient. If the fluid supply (e.g. water) reaches a predetermined upper temperature limit, for example about 80-110° F., a valve will switch and send the coolant to a liquid to air heat exchanger instead, as the induction drive 40 and induction coil 30 need to be cooled lower than about 110° F. In an embodiment disclosed, the actual temperature limits and set points may be adjusted to take into account operating conditions.

Tank Heating

The induction heater system 10 of the present disclosure may also be used to provide heated water or other heated fluids for downhole oil and gas operations, including but not limited to hydraulic fracturing. In such downhole frac operations, a relatively large volume of water is required, and is often stored in relatively large reservoirs (frac ponds, frac sumps, frac water tanks, frac water inflatable bags/bladders etc.) at the location where the frac operation is to be conducted, which may store millions of gallons of water in preparation for a frac operation. The presently disclosed system and method may be used to warm or heat a stream of water for the fracturing operation to avoid freezing in winter when the ambient temperature is below freezing. For example, a stream of water may be circulated from the storage tank, through an induction heater system of the present disclosure (and thus heated), and then back into the storage tank. In another example, water may be heated, real-time or on-demand, as it is used during the frac, for example to increase the temperature to some minimum to aid in blending water and frac additives. Similarly, the induction heater system of the present disclosure may be used to provide heated fluids (for example, but not limited to, water) for other processes, for example industrial process or construction or otherwise.

Pipeline Heating

Figure 8:
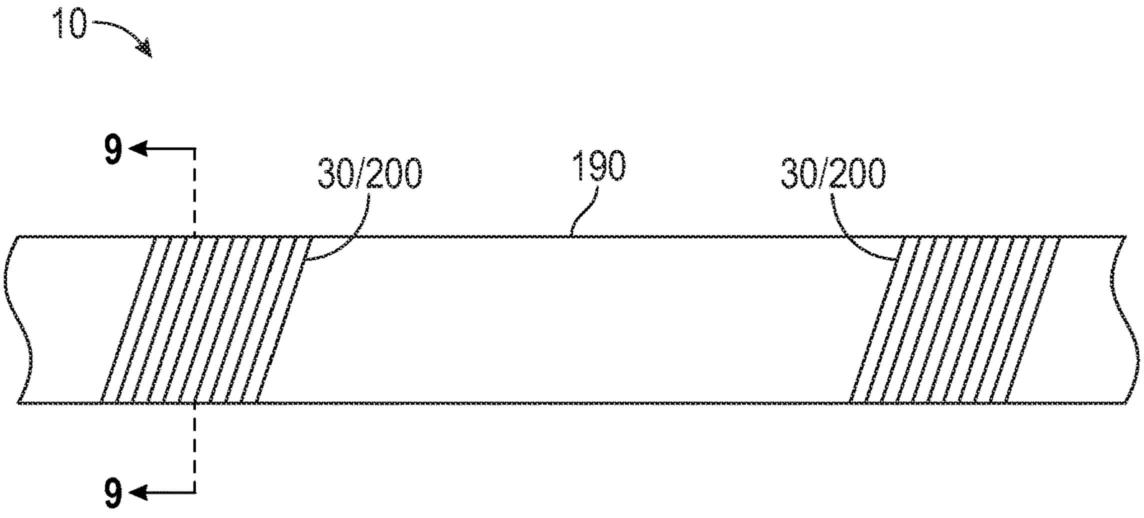
FIG. 8 is an embodiment of an induction heater system of the present disclosure.
Figure 9:
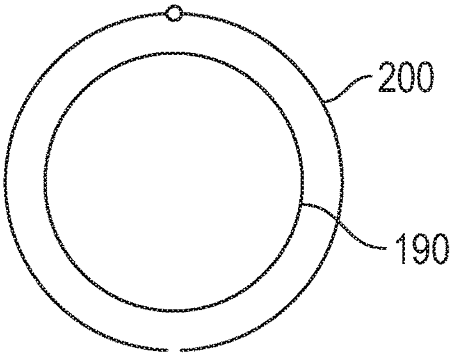
FIG. 9 is a cross-section of FIG. 8, along section 9-9.

Referring to FIGS. 8-9, the induction heater system 10 of the present disclosure may also be used to heat fluids flowing in a pipeline 190, for example oil, heavy oil, bitumen, or diluted bitumen. The induction heater system 10 may be used, for example, to mobilize paraffin wax to facilitate removal. The induction coil 30 may be a regular induction coil (e.g. one-piece) positioned on the pipeline during construction (or maintenance) or on a spool piece installed in the pipeline, or may be a split-type induction coil 200 (e.g. installed/assembled in pieces or sections around the pipeline) (see FIG. 9) which may be installed (or removed) more readily, for example any time after the pipeline has been built. The induction coil 30 may be installed sub-surface (e.g. in the pipeline trench) or may be installed on the surface (e.g. where the pipeline is above grade at storage facilities, pumping stations, meter stations, control valves, expansion loops, or specifically brought above grade for the induction heater system). The induction coil 30/split-type induction coil 200 are driven by an induction drive 40 (FIG. 5).

As the pipeline 190 may will experience natural cooling, induction heater systems 10 may be placed along the pipeline as needed to heat/re-heat the flowing fluid. In an embodiment disclosed, induction heater systems 10 may be installed every couple hundred meters or every kilometer or every few kilometers along the pipeline 190 as needed to keep the fluid (e.g. oil) warm enough to reduce its viscosity to flow or to heat the fluid above the melting point of a contaminant in the pipeline 190, for example paraffin wax, to melt the paraffin wax for removal from the pipeline. The induction heater systems 10 may be powered, for example, by a generator or a main power transmission line running along the pipeline. Using a pipeline for oil, heavy oil, bitumen, or diluted bitumen for example reduces the transport of such fluids by tanker truck or rail car and reduces the chances of spills while loading or unloading or in an accident, collision or derailment.

In an embodiment disclosed, the induction heater system 10 may be used to indirectly heat a pipeline 190, for example by circulating a heat transfer fluid such as a glycol/water mix or a heat transfer oil through the induction coil 30 to a heat exchanger associated with the pipeline 190, such as a heat transfer coil, to heat the pipeline 190 indirectly.

Concrete Mixing

In an embodiment disclosed, the induction heater system may be used to heat water for use in mixing concrete for a construction project, for example a dam, for example a hydroelectric dam. In an embodiment disclosed, water is drawn from a lake or a river or other water source and conveyed through the induction heater system 10 to provide heated water suitable for making concrete. In an exemplary embodiment, the water is heated to a concrete mixing temperature, for example about 176° F. (80° C.). In an embodiment disclosed, water may be heated from ambient conditions, just above freezing such as about 33.8° F. (1 degree Celsius). In an embodiment disclosed, water may be heated at a rate of between about 30 GPM and about 100 GPM.

Used Oil Recycling

Figure 10:
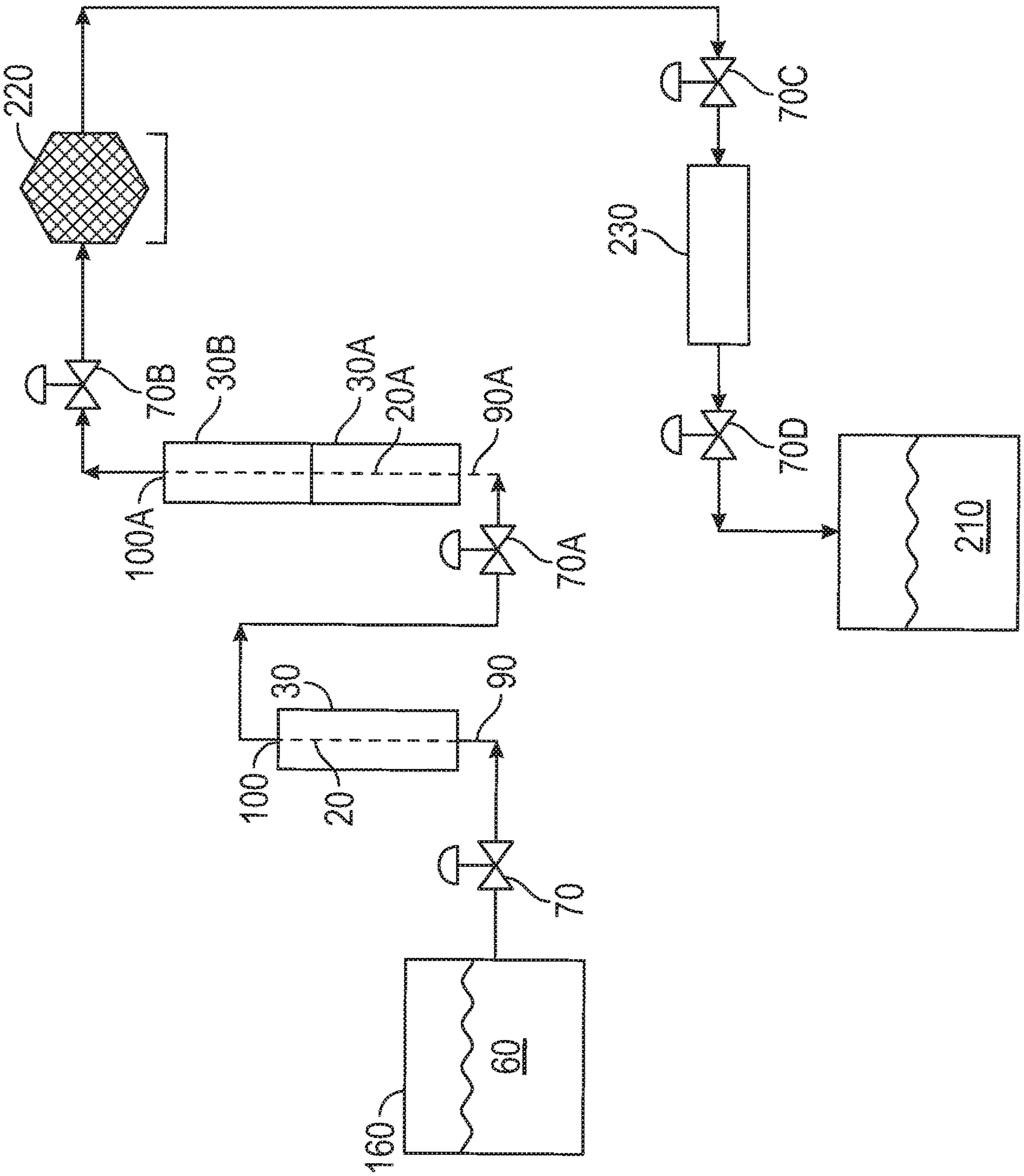
FIG. 10 is an embodiment of an induction heater system of the present disclosure.

Referring to FIG. 10, the induction heater system 10 may be used to heat fluid 60 (here used oil) to be processed to provide recycled clean oil 210.

In an embodiment disclosed, the used oil is conveyed from tank 160 through ferrous heat tube 20 heated by induction coil 30, and ferrous heat tube 20A heated by induction coils 30A, 30B. The used oil may be for example used motor oil, used gear oil, used hydraulic oil, or combinations thereof.

The heat tube 20 may be operated at a relatively low pressure or a negative pressure (less than about 0 psig) in order to facilitate at least partial vaporization of one or more components of the fluid 60 (used oil), for example lighter hydrocarbons, where the temperature at the outlet 100 may be about 450° F. However, at the outlet 100A, the temperature may be about 900° F. and the fluid 60 (used oil) substantially vapor. At those conditions, a number of the contaminants in the used oil break down.

The fluid 60 (now vapor) is conveyed through filter/screen/sieve 220 which filters/screen one or more contaminants. The filter/screen/sieve 220 may be between relatively coarse (e.g. like the screens of a shale shaker used in oil and gas drilling) and relatively fine (e.g. like a bag house filter used to filter particulate from flue gases). More than one filter/screen/sieve 220 may be used, and if so, more than one mesh/opening size may be used. The filter/screen/sieve 220 may be vibrated or otherwise cleaned periodically to remove residue/retentate. The fluid 60 (substantially vapor) is condensed via condenser 230 to provide recycled clean oil 210. One or more additives may be added to the recycled clean oil.

A controller 50 in association with induction drive 40 (FIG. 5) and one or more control valves 70, 70A, 70B,70C, 70D and 70E controls operation of the induction heater system 10.

Design

As used herein, ferrous includes ferrous materials and ferrous alloys, for example including carbon steel or stainless steels containing iron or thick graphite crucibles. A ferrous heat tube is one which components of may be heated by induction coil heating.

Induction coils at higher power levels are known to destroy welded pipe. However, in the present invention with lower power levels, the heat tube may be seamless or not seamless (e.g. welded seam). However, preferably, the heat tube is constructed of seamless pipe.

In the preceding description, for purposes of explanation, numerous details are set forth in order to provide a thorough understanding of the embodiments. However, it will be apparent to one skilled in the art that these specific details are not required. In other instances, well-known electrical structures and circuits are shown in block diagram form in order not to obscure the understanding.

The above-described embodiments are intended to be examples only. Alterations, modifications and variations can be effected to the particular embodiments by those of skill in the art. The scope of the claims should not be limited by the particular embodiments set forth herein, but should be construed in a manner consistent with the specification as a whole.

What is claimed is:

1. An induction heater system comprising:

a ferrous heat tube, having an inlet and an outlet;

a level instrument adapted to measure or indicate or both measure and indicate a liquid level in the ferrous heat tube;

an induction coil, extending around the ferrous heat tube;

an induction drive; and a controller, adapted to regulate operation of the induction drive, a fluid supply, and the liquid level, wherein a fluid conveyed through the ferrous heat tube and heated.

2. The induction heater system of claim 1, wherein the fluid is water or oil or combinations thereof.

3. The induction heater system of claim 2, the fluid supply comprising a pump and an inlet accumulator or a pump and a proportional controlled electric valve.

4. The induction heater system of claim 1, wherein the ferrous heat tube is carbon steel or iron containing stainless steel or alloys thereof.

5. The induction heater system of claim 4, wherein the ferrous heat tube comprises seamless pipe.

6. The induction heater system of claim 1, further comprising a preheater, the preheater comprising a heat rising recycle, the heat rising recycle comprising a pump or a flow restriction or both.

7. The induction heater system of claim 1, wherein the fluid is heated to at least partial vaporization.

8. The induction heater system of claim 7, wherein the ferrous heat tube is oriented generally vertically, between about +1-45° from vertical.

9. The induction heater system of claim 8, wherein the inlet is located substantially at a lower portion of the ferrous heat tube and the outlet is located substantially at an upper portion of the ferrous heat tube.

10. The induction heater system of claim 1, further comprising one or more ferrous insert within the ferrous heat tube.

11. The induction heater system of claim 9, the upper outlet further comprising an outlet accumulator pressure vessel or a vaporization vessel or condensing chamber.

12. The induction heater system of claim 1, wherein the level instrument comprises a wave guided radar level or a high pressure sight glass or both.

13. The induction heater system of claim 1, wherein the level instrument comprises a plurality of temperature transducers, extending along the ferrous heat tube to determine the liquid level.

14. The induction heater system of claim 13, the temperature transducers comprising thermocouples.

15. The induction heater system of claim 1, wherein the ferrous heat tube comprises a portion of a pipeline, the induction coil comprises a split induction coil, adapted to be installed on the pipeline, and adapted to heat the fluid inside the pipeline, wherein the fluid comprises oil, heavy oil, bitumen, diluted bitumen, paraffin wax or combinations thereof.

16. A method of producing heated fluid, comprising:

providing the induction heater system of claim 1;

receiving fluid from a fluid supply;

conveying the fluid through the ferrous heat tube, the ferrous heat tube heated by the induction coil extending around the ferrous heat tube, to provide the heated fluid;

driving the induction coil by the induction drive; and controlling the operation of the induction drive or the fluid supply or both.

17. The method of claim 16, wherein the fluid is water, oil, or combinations thereof.

18. The method of claim 17, wherein the fluid is water and the heated fluid is provided to an oil and gas well fracturing operation.

19. The method of claim 18, wherein the heated fluid is provided in substantially real-time.

20. The method of claim 17, wherein the fluid is water, and wherein the heated fluid is provided to a concrete mixing operation.

21. The method of claim 17, wherein the fluid is water, and wherein the water is heated to vaporization to provide steam.

22. The method of claim 21, wherein the steam is provided to an enhanced oil recovery process.

23. The method of claim 22, wherein the enhanced oil recovery process comprises steam assisted gravity drainage (SAGD), cyclic steam stimulation (CSS) or variations thereof.

24. The method of claim 17, wherein the ferrous heat tube comprises a pipeline segment, and wherein the fluid comprises oil, heavy oil, bitumen, diluted bitumen, paraffin wax or combinations thereof inside the pipeline.

25. The method of claim 17, wherein the fluid is used oil, and wherein the used oil is heated to vaporization to provide feedstock for an oil recycling operation.

26. An induction heater system comprising:

a ferrous heat tube, having an inlet and an outlet, wherein the ferrous heat tube is oriented generally vertically, between about +1-45° from vertical;

an induction coil, extending around the ferrous heat tube;

an induction drive;

a controller, adapted to regulate operation of the induction drive or a fluid supply or both; and a pivot mount proximate a lower end of the ferrous heat tube, the ferrous heat tube pivotable between a substantially vertical orientation and a substantially horizontal orientation about the pivot mount, wherein a fluid conveyed through the ferrous heat tube is heated to at least partial vaporization.

27. A method of descaling a substantially vertical ferrous heat tube to remove boiler scale, comprising:

providing the induction heater system of claim 1, wherein the ferrous heat tube is substantially vertical;

cooling the heat tube down to at least a predetermined safe temperature;

draining any fluid from the heat tube;

activating the induction coil to heat the ferrous heat tube to a predetermined maximum self-cleaning temperature to dry out the boiler scale, such that the boiler scale cracks and falls off the ferrous heat tube;

slowly cooling the ferrous heat tube down to at least the predetermined safe temperature; and removing the boiler scale from the ferrous heat tube.

28. The method of claim 27, wherein the maximum predetermined self-cleaning temperature is about 1000° F.

29. The method of claim 28, further comprising pivoting the substantially vertical ferrous heating tube into a substantially horizontal position prior to activating the induction coil to heat the ferrous heat tube to the predetermined maximum self-cleaning temperature.

* * * * *